United States Patent [19]

Winter et al.

[11] 4,047,690
[45] Sept. 13, 1977

[54] MOLD FOR CONCRETE TEST CUBE

[75] Inventors: Wilhelm Winter; Artur Held, both of Frankfurt am Main, Germany

[73] Assignee: FORM-PLAST GmbH, Frankfurt-Kalbach, Germany

[21] Appl. No.: 563,375

[22] Filed: Mar. 31, 1975

[30] Foreign Application Priority Data

Apr. 3, 1974 Germany ............................ 117467

[51] Int. Cl.² ............................ B28B 7/08; B28B 7/12
[52] U.S. Cl. ................................ 249/66 A; 249/134; 249/137; 249/DIG. 4
[58] Field of Search ................... 249/66 A, 137–138, 249/117, DIG. 4, 173, 134; 425/437, 439, DIG. 44; 264/313, 335; 220/DIG. 1

[56] References Cited

U.S. PATENT DOCUMENTS

| 1,134,051 | 3/1915 | Long et al. | 249/48 |
|---|---|---|---|
| 1,478,746 | 12/1923 | Kinton et al. | 249/137 |
| 2,071,621 | 2/1937 | Gettelman | 220/DIG. 1 |
| 2,139,191 | 12/1938 | Jung | 249/137 |
| 2,148,084 | 2/1939 | Nock | 425/437 |
| 2,473,748 | 6/1949 | Green | 249/137 |
| 3,163,908 | 1/1965 | Lawmaster | 249/164 |
| 3,353,220 | 11/1967 | Lenoble | 264/313 |
| 3,572,625 | 3/1971 | Williamsen | 249/117 |

Primary Examiner—Francis S. Husar
Assistant Examiner—John McQuade
Attorney, Agent, or Firm—Edward E. Sachs

[57] ABSTRACT

A mold for concrete test cubes of plastic-like material having a vertically extending enclosure and, about midway, radially projecting impact ledges and at the top of the enclosure vertical spacers in the form of legs or extensions of wall panels.

6 Claims, 3 Drawing Figures

MOLD FOR CONCRETE TEST CUBE

The present invention relates generally to a mold for casting concrete test cubes. Conventionally, such cubes are formed for testing the compressive strength of cast concrete in special test laboratories. The term "test cube" as used in the trade also encompasses other geometric configurations, the most common of which is a cylinder. The term "test cube" is used herein in a similar non-restrictive manner.

In the prior art such molds are usually made of metal. In order to facilitate the removal of the cast test cubes it has heretofore been necessary to construct the mold as a multi-part structure which can be taken apart to release the cast cube. The construction and handling of such a mold is not very economical since considerable time has to be spent on these efforts and on the removal of the concrete residue on the mold walls.

It is therefore the primary object of the present invention to provide a mold for test cubes which is of unitary construction and made of plastic to overcome the shortcomings of prior art devices.

An aspect of the present invention resides in providing a mold for so-called concrete test cubes, which is composed of a unitary vertically extending wall which defines a tubular enclosure having a first projection which extends angularly, i.e., sideways, from the enclosure, on the outside thereof, to provide an impact surface when the enclosure is tilted from a vertical to a substantially horizontal position. The enclosure further includes at least two vertically extending projections arranged substantially diametrically opposite each other and formed on the top surface of the enclosure, and a bottom panel secured to the bottom of the enclosure and having an opening provided therein. The panel and the enclosure are formed of plastic or plastic-like material.

For a better understanding of the present invention, together with other and further objects thereof, reference is had to the following description taken in connection with the accompanying drawings, and its scope will be pointed out in the appended claims.

Figure 1:
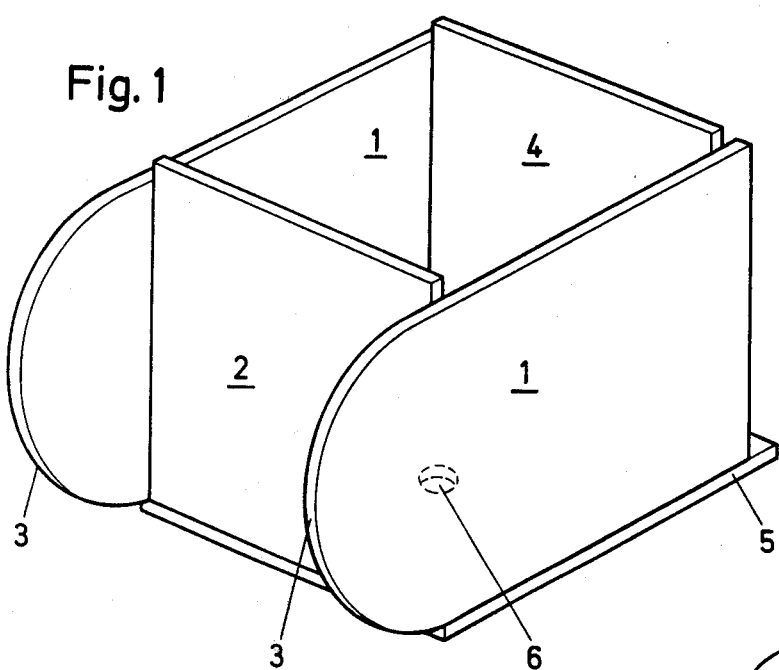
FIG. 1 is a perspective view of the device in accordance with the present invention.

Referring now to the drawings, there is shown a mold of a one-piece, i.e., unitary, construction which is formed of a suitable synthetic material, such as plastic, and includes, see FIG. 1, sidewalls 1 projecting beyond a forward wall 2 and form at each terminal end a semi-circular tilting member. Parallel to the forward wall 2 there is arranged a rear wall 4, both of these walls are slightly higher than sidewalls 2. The walls 1, 2 and 4 form an enclosure as shown in FIG. 1, with the bottom thereof being closed by a panel 5 provided with a valve or hose opening 6.

The mold of synthetic or plastic-like material established heat storage during the exothermic bonding or setting of the concrete, even when the mold with the test cube is submerged in water. This permits a complete bonding so that comparable, reproducible load factors can be measured on the test cube. The heat storage increases the reaction speed and reduces the time required for bonding.

Figure 2:
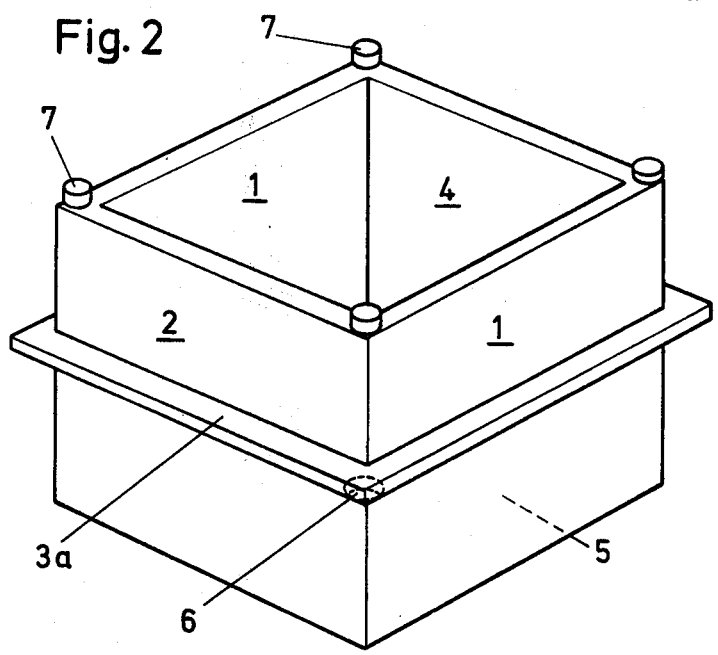

In FIG. 2, there is shown a modification of the device shown in FIG. 1. Herein, the walls 1,2,4 are surrounded, elevationally about midway, by a circumferentially extending continuous strip 3a and on the top edge of the four side walls panels (1,2 and 4), at the four corners of the mold, there are formed four spacer legs 7. After the mold has been filled with cement, the concrete is leveled between the spacers 7 to provide a smooth surface which is flush with the top margin of the walls.

Figure 3:
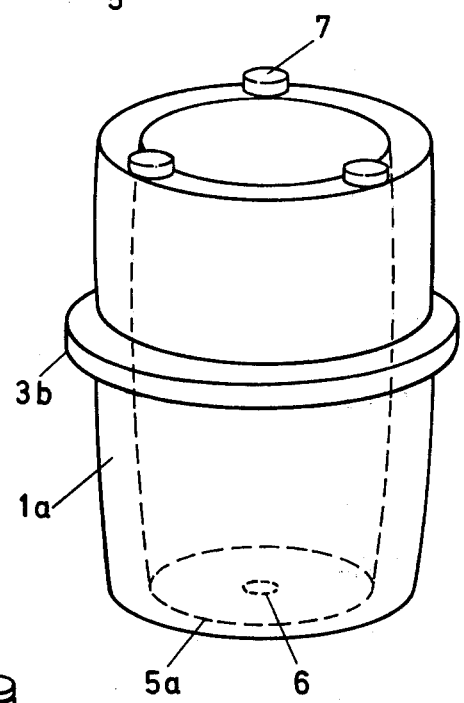
FIGS. 2 and 3 are views similar to FIG. 1, showing modifications of the invention illustrated in FIG. 1.

The mold shown in FIG. 3 is a modification of the device shown in FIG. 2. Herein, wall forms a single, continuous circular structure.

In lieu of the valve (not shown), the opening 6 may be covered by a plastic cap. In operation, after the concrete has set, the mold is simply lifted, or kicked, so that the mold is tilted and falls sideways and comes to bear against the strip 3a, or projection 3, and then is tilted further until the mold is completely upside down with bottom panel 5 now being at the top. The impact is usually sufficient to loosen the finished test cube with the smooth plastic mold, and the cube can move downward a little due to the positioning of the spacers 7, or the equivalent projections of panels 2 and 4.

Preferably, a hose with air or water is now placed into the opening 6 which causes the cube to further separate from the mold. At the same time, loose concrete particles within the mold (if any) can be flushed out and the mold is immediately usuable again.

In operation, using the device shown in FIG. 1, the rounded projections 3 facilitate the tilting of the mold in a rolling contact manner. While projections 3 require that the tilting be started by exerting forces against the rear wall 4, in the modification according to FIG. 2, these forces may be placed against any side panel (1,2,4). In either case, the two step approach is quite effective to separate the cast cube from the mold.

While there have been described what are at present considered to be the preferred embodiments of this invention, it will be obvious to those skilled in the art that various changes and modifications may be made therein without departing from the invention, and it is aimed, therefore, in the appended claims to cover all such changes and modifications as fall within the true spirit and scope of the invention.

I claim:

1. A mold for concrete test cubes, comprising:
   a vertically extending wall defining a tubular enclosure,
   a flange-like first impact projection extending angularly from the enclosure on the outside thereof and located spaced from the bottom of the enclosure, said flange-like projection constituting the only substantial projection beyond the enclosure between the top and bottom thereof, the first projection forming an impact surface when said enclosure is tilted from a vertical to a substantially horizontal position; at least three vertically extending second impact projections formed on the top end of the enclosure, said second projections being relatively small and effective to permit a multidirectional planar smoothing of substantially the whole upper surface of the concrete test cube prior to solidification;
   and a bottom panel secured to the bottom of the enclosure and having an opening provided therein; said panel and said enclosure being formed of plastic or plastic-like material as an integrally connected single piece construction.

2. A mold according to claim 1, wherein said enclosure comprises rear, forward and side panels.

3. A mold according to claim 1, wherein said first projection is a substantially continuous and peripherally extending strip extending around the enclosure about vertically midway.

4. A mold according to claim 1, wherein said second projections are at least four spacers.

5. A mold according to claim 4, wherein said enclosure has a rectangular cross-section providing for four corners and said spacers are narrow legs formed equidistantly from each other on the corners of the enclosure.

6. A mold according to claim 1, wherein said enclosure in cylindrical.

* * * * *